US007666683B1

(12) United States Patent
Cole (10) Patent No.: US 7,666,683 B1
(45) Date of Patent: Feb. 23, 2010

(54) RAPID METHOD OF DIAGNOSING A NORMAL PREGNANCY WITH HIGH ACCURACY

(75) Inventor: Laurence A. Cole, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 788 days.

(21) Appl. No.: 11/250,050

(22) Filed: Oct. 13, 2005

Related U.S. Application Data (60) Provisional application No. 60/618,433, filed on Oct. 13, 2004, provisional application No. 60/621,512, filed on Oct. 22, 2004, provisional application No. 60/651,832, filed on Feb. 10, 2005, provisional application No. 60/627,904, filed on Nov. 15, 2004.

(51) Int. Cl.
*G01N 33/48* (2006.01)
*G01N 33/76* (2006.01)
(52) U.S. Cl. .............................. 436/65; 436/63; 436/86; 436/87; 436/164; 436/172; 435/7.1; 435/7.94
(58) Field of Classification Search .................. 436/63, 436/65, 86, 87, 164, 172, 514, 518; 435/7.1, 435/7.94
See application file for complete search history.

(56) References Cited

U.S. PATENT DOCUMENTS

| 5,786,220 | A | * | 7/1998 | Pronovost et al. ............ 436/518 |
| 6,339,143 | B1 | | 1/2002 | Krichevsky et al. |
| 6,429,018 | B1 | | 8/2002 | Cole et al. |
| 6,500,627 | B1 | | 12/2002 | O'Connor et al. |
| 6,627,457 | B2 | | 9/2003 | Pandian et al. |
| 7,439,026 | B2 | * | 10/2008 | Pandian et al. ................ 435/7.1 |
| 2003/0153093 | A1 | * | 8/2003 | Chang et al. ................. 436/510 |
| 2005/0148096 | A1 | * | 7/2005 | Cole et al. ................... 436/510 |
| 2006/0063275 | A1 | * | 3/2006 | Cole et al. ................... 436/510 |

FOREIGN PATENT DOCUMENTS

WO       98/23300    *   6/1998

OTHER PUBLICATIONS

U.S. Appl. No. 11/144,091, filed Jun. 2, 2005, Cole.
Cole, LA, Urine β-core fragment, a potential screening test for ectopic pregnancy and spontaneous abortion. *Fetal Diagnosis and Therapy*, 12:336-339, 1997.
Cole, LA, ITA hCG (Invasive Trophoblast Antigen, hyperglycosylated hCG) the Optimal Antigen in Pregnancy Testing. *Clinical Biochemistry*, 36(8):647-55 Nov. 2003.
Saxena BB, Hasan SH, Haour F, Schmidt-Gollwitzer M. Radioreceptor Assay of human chorionic gonadotropin: Detection of Early Pregnancy. Science 1974; 184:793-5.
Braunstein GD, Rasor J, Adler D, Danzen H, and Wade ME. Serum human chorionic gonadotropin levels throughout normal pregnancy. Am J Obstet Gynecol 1976; 126: 678-681.

Gasser RF. 1981. Embryology and fetology. In *Principles and Practice of Obstetrics and Perinatology*, vol. 1, edited by Iffy L, Kaminetzky HA (New York; John Wiley & Sons), pp. 127-180.
Lenton EA, Grudzinskas JG, Neal LM, Chard T, Cooke ID. Chorionic gonadotropin concentrations in early human pregnancy: Comparisons of specific and nonspecific assays. Fertil Steril 1981; 35: 40-5.
Wilcox AJ, Baird DD, Dunson D, McChesney R, Weinberg CR. Natural limits of pregnancy testing in relation to the expected menstrual period. JAMA 2001; 286: 1759-61.
Wilcox AJ, Weinberg CR, O'Connor JF, Baird DD, Schlatterer JP, Canfield RE, et al. Incidence of early loss of pregnancy. N. Engl J Med 1988; 319: 189-94.
Pittaway DE and Wentz AC. Evaluation of early pregnancy by serial chorionic gonadotropin determinations: A comparison of methods by receiver operating characteristic curve analysis. Fertil Steril 1985; 43: 529-533.
Braunstein GD, Grodin JM, Vaitukaitis J, Ross GT. Secretory rates of human chorionic gonadotropin by normal trophoblast. Am J Obstet Gynecol 1973; 115: 447-50.
Barnhart K, Sammel MD, Chung K, Zhou L, Hummel AC, Wensheng Gou. Decline of serum human chorionic gonadotropin and spontaneous abortion: Defining the normal curve. Obstet Gynecol 2004; 104: 975-81.
Liu HC, Davies 0, Berkeley A, Graf M, Rosenwaks Z. Late luteal estradiol patterns are a better prognosticator of pregnancy outcome than serial beta-human chorionic gonadotropin concentrations. Fertil Steril 1991; 56: 421-6.
Cowan BD. Ectopic Pregnancy. Curr Op Obstet Gynecol 1993; 5: 328-32.
Abrar N. (May 2004) "Miscarriage: The Incidence of miscarriage" Retrieved Dec. 9, 2004, from ivf-infertility.com.
Sepilian V. (Nov. 2004) eMedicine Specialties: Obstetrics and Gynecology. "Ectopic Pregnancy." Retrieved Dec. 9, 2004, from emedicine.com.

(Continued)

*Primary Examiner*—Maureen M Wallenhorst
(74) *Attorney, Agent, or Firm*—Henry D. Coleman; R. Neil Sudol; William J. Sapone (57) ABSTRACT

The present invention relates to a novel method of determining the existence of a normal pregnancy which has a high likelihood of culminating in a term pregnancy, by measuring hyperglycosylated hCG in a pregnant woman and comparing the concentration of measured hyperglycosylated hCG with a predetermined value. A measurement of hyperglycosylated hCG above the predetermined value, for example, about 13 ng/ml, is evidence of a high likelihood of a normal pregnancy. A measurement below the predetermined value is evidence of an abnormal pregnancy (ectopic pregnancy or miscarriage). Further analysis of the patient in the event that the measurement falls below the predetermined value is made by intravaginal or abdominal ultrasound to determine whether or not the pregnancy is ectopic or will likely result in a spontaneous abortion (miscarriage). This point-of-care (POC), over-the-counter (OTC) or professional laboratory application is unexpectedly rapid and highly predictive of pregnancy outcome in women exhibiting symptoms of pregnancy.

40 Claims, 3 Drawing Sheets

OTHER PUBLICATIONS

Jones RE. 1991. Pregnancy, Spontaneous Abortion. In *Human Reproductive Biology*, edited by Richard E. Jones. (San Diego, CA, Academic Press, Inc.), pp. 189-228.

Heffner LJ. 2001. Pregnancy complications, early pregnancy loss. In *Human Reproduction at a Glance*, edited by Blackwell Sciences editorial offices (Berlin, Germany, Blackwell Science Ltd.). pp. 86-91.

Cole LA. The O-Linked Oligosaccharide structure are striking different on pregnancy and choriocarcinoma hCG. J Clin Endocrinol Metab 1987; 65: 811-3.

Amano J, Nishimura R, Mochizuki M, Kobata A. Comparative study of the mucin-type sugar chains of human chorionic gonadotropin present in the urine of patients with trophoblastic diseases and healthy pregnant women. J Biol Chem 1988; 263: 1157-65.

Elliott MM, Kardana A, Lustbader JW, Cole LA. Carbohydrate and peptide structure of the alpha- and beta-subunits of human chorionic gonadotropin from normal and aberrant pregnancy and choriocarcinoma. Endocrine 1997; 7: 15-32.

Birken S, Krichevsky A, O'Connor J, Schlatterer J, Cole L, Kardana A, Canfield R. Development and characterization of antibodies to a nicked and hyperglycosylated form of hCG from a choriocarcinoma patient: Generation of antibodies that differentiate between pregnancy and choriocarcinoma hCG. Endocrine 1999; 10: 137-44.

Pandian R, Lu J, and Ossolunska-Plewnia J. Fully automated chemiluminometric assay for hyperglycosylated human chorionic gonadotropin (invasive trophoblast antigen). Clin Chem 2003; 49: 808-10.

Cole LA ,Sutton JM, Higgins TN. Higgins, Cembrowski GS. Between-method variation in hCG test results, Clin Chem, 2004; 50:874-882.

Cole LA, Khanlian SA, Sutton JM, Davies S, Stephens ND. Hyperglycosylated hCG (invasive trophoblast antigen, ITA) a key antigen for early pregnancy detection. Clin Biochem 2003; 36: 647-55.

Kovalevskaya G, Birken S, Kakuma T, O'Connor JF. Early pregnancy human chorionic gonadotropin isoforms measured by an immunometric Assay for Choriocarcinoma-like hCG. J Endocrinol 1999; 161: 99-106.

Kovalevskaya G, Genbacev O, Fisher SJ, Caceres E, O'Connor JF. Trophoblast Origin of hCG Isoforms: Cytotrophoblasts are the primary Source of Choriocarcinoma-like hCG. Mol Cell Endocrinol 2002; 194: 147-55.

Kovalevskaya G, Birken S, Kakuma T, Osaki N, Sauer M, Lindheim S, et al. Differential expression of human chorionic gonadotropin (hCG) Glycosylation Isoforms in failing and continuing Pregnancies: Preliminary characterization of the hyperglycosylated hCG Epitope. J Endocrinol 2002; 172: 497-506.

O'Connor JF, Ellish N, Kakuma T, Schlatterer J, Kovalevskaya G. Differential Urinary gonadotropin profiles in early pregnancy and early pregnancy loss. Prenat Diagn 1998; 18: 1232-40.

Carmona F, Balasch J, Creus M, Fabregues F, Civico S, Vidal E, et al. Early hormonal marker of pregnancy outcome after in vitro fertilization and embryo transfer. J Assist Reprod Genet 2003; 20: 521-26.

Urbancsek J, Hauzman E, Fedorcsak P, Halmos A, Devenyi N, Papp Z. Serum human chorionic gonadotropin measurements may predict pregnancy oucome and multiple gestations after in vitro fertilization. Fertil Steril 2002; 78: 540-42.

Cole, L.A., Shahabi, S., Oz, U.A., Bahado-Singh, R.O., and Mahoney, M.J. Hyperglycosylated hCG (Invasive Trophoblast Antigen) Immunoassay: a New Basis for Gestational Down Syndrome Screening. Clin. Chem. 45:2109-2119, 1999.

* cited by examiner

RAPID METHOD OF DIAGNOSING A NORMAL PREGNANCY WITH HIGH ACCURACY

RELATED APPLICATIONS

This application claims the benefit of priority from provisional application U.S. 60/618,433, filed Oct. 13, 2004; U.S. 60/621,512, filed Oct. 22, 2004; U.S. 60/627,904, filed Nov. 15, 2004 and U.S. 60/651,832, filed Feb. 10, 2005, which applications are incorporated by reference in their entirety herein.

FIELD OF THE INVENTION

The present invention relates to a novel method of measuring hyperglycosylated hCG in pregnant women to make the determination as to the outcome of the pregnancy, i.e., to determine that the pregnancy has a high likelihood of being a normal pregnancy and will go to term. The present method allows a rapid determination (in a matter of a few minutes) with high accuracy whether a pregnancy is normal or may be at risk. This method is preferably provided as a point-of-care (POC) or over-the-counter application and is unexpectedly rapid and highly predictive of a normal pregnancy outcome in women who are pregnant.

Ancillary to the first aspect of the present invention, the present invention also relates to a novel method of combining a measurement of hyperglycosylated hCG in pregnant women with transvaginal ultrasound and/or abdominal ultrasound to make a rapid determination (in a matter of a few hours at most) with high accuracy whether a pregnancy is ectopic or not (normal). This point-of-care (POC) application is unexpectedly rapid and highly predictive of pregnancy outcome in women exhibiting symptoms of ectopic pregnancy.

BACKGROUND OF THE INVENTION

Pregnancy in human females can be terminated by unfortunate circumstances, including ectopic pregnancy and spontaneous abortion. Likewise, knowing that a pregnancy is a normal pregnancy with a high likelihood that it will go to term is important, especially to woman who have had previous pregnancies terminated by spontaneous abortion. Detection of the likelihood of either ectopic pregnancy or spontaneous abortion occurring is important to the pregnant woman, in the case of ectopic pregnancy to provide for rapid therapeutic intervention, and in the case of spontaneous abortion to provide an ability to prepare psychologically for the abnormal pregnancy. Failure to diagnose ectopic pregnancy can be harmful and even fatal to the pregnant woman. Yet, it is also highly desirable to distinguish between abnormal pregnancies (i.e., ectopic pregnancies and pregnancies which will spontaneously abort) and normal pregnancies so that desirable normal pregnancies are not needlessly terminated.

Spontaneous abortion is a major health concern to women, affecting about 20% of couples wishing to have children. The diagnostic evaluation of spontaneous abortion is extensive and complex, with many different etiologies, each causing a small proportion of the total cases. The etiologies can be grouped into five categories: anatomic, infectious, hormonal, immunological, and genetic, thereby requiring the collaborative efforts of many medical specialists. Despite such thorough (and expensive) diagnostic workups, it has been estimated that the specific cause for spontaneous remains unknown in a relatively large percentage of affected women (Stephenson, *Fertil. Steril.* 66:24 (1996).

It is known that if a pregnant woman suffers a spontaneous abortion then any subsequent pregnancies which that woman may have are also more likely to result in spontaneous abortions. The precise reason why certain women suffer such spontaneous abortions is not known but an immunological defect is suspected in many cases of recurrent spontaneous abortion for which no underlying genetic, hormonal, microbiological or anatomical abnormality has been detected. This defect is believed to be related to a failure of maternal immune recognition of the implanting blastocyst, which results in the lack of production of protective factors and subsequent rejection of the developing foetal trophoblastic tissue at maternal-foetal interfaces. Pregnancy outcome for these women is especially precarious and attempts to provide some insight into the outcome of pregnancy would be desirable benefit for these women.

The incidence of ectopic pregnancy in the United States has risen 6-fold in the last three decades. According to the 2002 American College of Obstetrics and Gynecology Survey, ectopic pregnancies now account for about 2.1% of reported pregnancies. Despite the available knowledge with regard to progesterone and hCG levels in pregnant females, rapid screening tests at the point of care for confirming the existence or likelihood of an ectopic pregnancy or spontaneous abortion are not generally available. Thus, it would be desirable to provide rapid screening assays which could be utilized in blood, plasma, serum or urine samples from the pregnant female to confirm the continuing normal nature of the pregnancy or to assess the likelihood of an abnormal pregnancy, i.e., an ectopic pregnancy or spontaneous abortion. Diagnostic tests are now needed to identify a normal or abnormal pregnancy at an early stage rapidly and to a high degree of certainty, especially when a pregnant woman has experienced recurring spontaneous abortion or the patient exhibits symptoms of ectopic pregnancy or other complications of pregnancy before it is clinically evident. Such tests should be rapid, highly accurate and preferably taking no more than an hour or less to run, and should be convenient so that the tests could be performed at the point of care.

This would be useful in all pregnancies and especially those in pregnant women who have had at least one spontaneous abortion. This would also be useful at point-of-care facilities or in home pregnancy tests. Presented with possible complications of pregnancy, the ER or point-of-care physician would among other tests perform a POC hCG pregnancy test as well as a test to determine pregnancy outcome, i.e., to determine the likelihood that any pregnancy is a normal pregnancy or abnormal pregnancy (e.g., ectopic or spontaneous abortion). If the pregnancy test is positive, it would then be a case of trying to differentiate a normal intrauterine pregnancy from an extrauterine pregnancy (ectopic) or a pregnancy likely to result in a spontaneous abortion. There are approximately 100,000 proven ectopic pregnancies (in 5 million pregnancies) in the USA each year and up to a million or more pregnancies which spontaneously abort. The incidence (actual numbers) of these pregnancies is much higher outside the United States.

Currently, there is no single fast, accurate assay for assessing a normal pregnancy outcome at an early stage in a pregnant woman. There are complicated tests for determining the existence of ectopic pregnancy. In the case of ectopic pregnancy, the approach for determining its existence requires that a woman who presents with ectopic pregnancy consistent symptoms undergoes a two-step analysis which uses transvaginal ultrasound coupled with an hCG doubling test to evidence the existence of ectopic pregnancy. In the case of transvaginal ultrasound, this is used to see if there is evidence of a fetus by looking for a fetal sac. A transabdominal ultrasound may be used to see if there is evidence of ectopic pregnancy. The problem with using this approach is in early pregnancies the fetus or fetal sac, at 5-8 weeks or pregnancy (usually, about 1-4 weeks after missing of menses), the time when symptomology of ectopic pregnancy first becomes evident, is miniscule and may often be missed using ultrasound. In addition to the use of transvaginal ultrasound, the analysis also relies on the use of the hCG doubling test to see if serum hCG results double or more than double in 2 days. If hCG does not double within the two day period, that is an indicator of ectopic pregnancy. In contrast, in the case of spontaneous abortion, there is no current approach for determining its likelihood.

As described above, the conventional approach(es) for differentiating a normal pregnancy from an abnormal pregnancy, whether that abnormal pregnancy is an extraurterine ectopic pregnancy or a spontaneous abortion are either deficient, or, in the case of spontaneous abortion, virtually non-existence. As such, mistakes are often made and normal and abnormal pregnancies are wrongly diagnosed. With respect to woman who have had at least one spontaneous abortion, determining that a pregnancy at an early stage is a normal pregnancy is an important issue. Another important issue is to identify the likelihood of abnormal pregnancy, rapidly and with a high degree of accuracy, so that monitoring of the pregnancy or treatment may begin expeditiously.

Human chorionic gonadotropin (hCG), a glycoprotein hormone, exists in pregnancy urine and serum as early as the week following implantation (1-6). Maternal concentrations of hCG are widely used as a means of distinguishing normal and abnormal pregnancies, with the concentration of maternal hCG reportedly doubling approximately every 2 days in the first 2 months of a favorable outcome gestation (7-9). Measuring the hCG doubling rate over 2 days has become a standard part of prenatal care. Falling serum hCG results, or concentrations that do not double within two days, are used to indicate a failing pregnancy, either a spontaneous abortion in the first trimester of pregnancy or ectopic pregnancy. hCG levels that at least double over 2 days indicate a favorable outcome pregnancy, that likely will go to term (9). Early identification of a failing pregnancy can help ensure proper care and management; this is particularly crucial in the case of an ectopic pregnancy.

The hCG doubling (in two days) test is, however, as explained above, awkward. Firstly, the need to make two office/clinic visits, to order the test and discuss the result with the physician. Secondly, by the need to make 2 laboratory visits or have 2 blood draws over exacting times. Furthermore, as reported, this test is limited in sensitivity (depending on the report, 62-78%), and by a high rate of false-positive rate (26-40%) (10-11). It is the experience of the University of New Mexico Reproductive Endocrinology Clinic, for instance, that this test detects 73% of failures at a 40% false-positive rate (Byrn et al., unpublished data). Considering the reported risks in the USA of spontaneous abortion and ectopic pregnancy (12-15), this test has a predictive value positive (for pregnancy failures) of 35%. Much more accurate tests are needed to assess risk of pregnancy failure and favorable outcomes, preferably with greater ease-of-use.

Hyperglycosylated hCG ("H-hCG") is an hCG molecule with additional sugar residues on its oligosaccharide side chains (16-18). Specific antibodies have been raised against H-hCG and assays have been established to detect only H-hCG (19). An FDA-approved automated chemiluminescence immunoassay for H-hCG is now available commercially, and used throughout the USA (20).

H-hCG has been shown by multiple authors to be the predominant form of hCG present in serum and urine samples in early pregnancy, during the time when implantation is occurring and the month that follows (21-26). It has been previously shown that significantly lower proportions of H-hCG (vs. hCG) are found in spontaneously aborting and ectopic pregnancies (25, 26). Considering the lower concentrations of hCG in failing pregnancies (7, 8, 10, 11), and the lower proportions of H-hCG (16-18), measurement of H-hCG concentrations may provide an amplified means of detecting failing pregnancies. However, no parameters have be described for measuring H-hCG to differentiate favorable outcome and pregnancy failure.

The present invention is directed to improved means for evaluating pregnancy outcome. We investigated H-hCG measurement protocols for serum and urine samples. Urine for potential over-the-counter and point-of-care applications and serum for point-of-care and professional laboratory applications. Urine samples are preferably those obtained initially upon waking of the patient/subject. Sensitivity. specificity, predictive values and diagnostic accuracy are assessed of single sample H-hCG measurements, and compared with analogous hCG results.

OBJECTS OF THE INVENTION

It is a primary object of the present invention to provide a method of rapidly and accurately determining the likelihood of a normal pregnancy at an early stage of pregnancy.

It is yet another object of the invention to provide a method of rapidly and accurately determining the likelihood of a normal pregnancy in women who have had pregnancies terminated by spontaneous abortion.

It is an additional object of the invention to rapidly and accurately the likelihood of an abnormal pregnancy in a patient so that the patient may be monitored for further developments of that pregnancy, including an ectopic pregnancy and spontaneous abortion.

It is still a further object of the invention to provide a test which may be used in a point-of-care facility, in an over-the-counter home pregnancy test, or in a professional laboratory setting to determine the existence of a normal or abnormal pregnancy.

It is yet another object of the present invention to provide a method of rapidly and accurately diagnosing an ectopic pregnancy in a patient preferably at a point of care, for example, in an emergency room, doctor's office or clinic.

It is still an additional object of the invention to rapidly and accurately diagnose ectopic pregnancy in a pregnant woman exhibiting symptoms of ectopic pregnancy so that rapid intervention/therapy may be afforded.

It is yet a further aspect of the invention to provide a two-part diagnosis of ectopic pregnancy at the point of care for a patient exhibiting symptoms of ectopic pregnancy.

Any one of these and/or other objects of the invention may be readily gleaned from the description of the invention which follows.

BRIEF DESCRIPTION OF THE INVENTION

The present invention relates to a method for identifying the existence of a normal or abnormal pregnancy (ectopic pregnancy or spontaneous abortion) with high accuracy at an early stage of pregnancy (detection range is preferably from about 4 or 5 weeks 0 days to about 8 weeks 0 days or later (for example, 9 weeks, 0 days or even 10 weeks, 0 days or more), or about the $1^{st}$ to the $4^{th}$ or $5^{th}$-$6^{th}$ week or later following the missing of menses) comprising in any order:

i. collecting a sample of whole blood, serum or urine from a female patient who is experiencing symptoms associated with pregnancy;

ii. measuring the concentration of hCG and/or hyperglycosylated hCG (H-hCG—also, invasive trophoblast antigen) in said sample to determine whether or not the patient is pregnant; and iii. if the measurement from step ii evidences pregnancy, separately measuring the concentration of hyperglycosylated hCG in a sample of whole blood, serum or urine from said patient and comparing the measurement of hyperglycosylated hCG with a predetermined value, preferably 13 ng/ml, wherein a measurement of more than the predetermined value indicates the likelihood of a normal pregnancy and wherein a measurement of less than a predetermined value indicates the likelihood of an abnormal pregnancy, generally either an ectopic pregnancy or a pregnancy which will terminate by spontaneous abortion. In the event that the analysis predicts an abnormal pregnancy, the patient should undergo a transvaginal ultrasound, an abdominal ultrasound or both a transvaginal and abdominal ultrasound on said patient to determine the existence of an ectopic pregnancy. If the ultrasound(s) evidences no ectopic pregnancy, then the method predicts that the pregnancy will spontaneously end (spontaneous abortion).

In this first aspect of the present invention, steps i and ii may be eliminated if it is already known that the patient is pregnant or if H-hCG is used to determine that the patient is pregnant, in which case the method relates to the collecting of a sample of blood, serum or urine from the patient and determining the levels of H-hGG in that sample, wherein a determined level of H-hCG above a predetermined level is indicative of a normal pregnancy, and wherein a determined level of H-hCG below a predetermined level is indicative of an abnormal pregnancy, i.e., an ectopic pregnancy or a spontaneous abortion. It is noted that the existence of pregnancy may be determined by solely measuring H-hCG levels, for example, as taught by Pandian, et al., U.S. Pat. No. 6,627,457, relevant portions of which are incorporated by reference herein or alternatively, by measuring both hCG and H-hCG (preferably, equally). In those methods which measure H-hCG in serum, urine or blood of a patient to determine pregnancy, that measurement of H-hCG can be compared with the predetermined value without having a further sample taken from the patient.

Regardless of which sample is used, if the H-hCG level in the sample is determined to be below the predetermined level, then a determination will be made using ultrasound to determine if the pregnancy is an ectopic pregnancy. In the absence of evidence of an ectopic pregnancy in the patient, spontaneous abortion will be the likely end result of the pregnancy.

The present method provides a rapid and accurate determination of the likelihood of a normal or abnormal pregnancy (i.e., an ectopic pregnancy or spontaneous abortion) in a female patient in as little as 10-30 minutes, preferably at a point-of-care facility or at home. Further analysis (especially a transvaginal and/or abdominal ultrasound) as described below may evidence the existence of an ectopic pregnancy wherein the patient may be treated surgically or with an abortefacient, as described herein.

In another method of the present invention, the state of a pregnancy of a pregnant patient may be determined at an early stage (e.g. about 4-9 weeks or more after the patient's last menses) by diagnosing the pregnancy as normal or as abnormal by applying steps comprising:

i. collecting a sample of whole blood, serum or urine from said pregnant woman; and ii. measuring the concentration of hyperglycosylated hCG in said sample; wherein a concentration of hyperglycosylated hCG in said sample of more than a predetermined value, preferably about 13 ng/ml, is indicative of a normal pregnancy and a concentration of less than the predetermined value, preferably, about 13 ng/ml, is indicative of an abnormal pregnancy. In certain preferred aspects of the present invention the method is performed on a pregnant woman who has had at least one previous pregnancy terminated by spontaneous abortion to determine the likelihood that the present pregnancy is normal, wherein a measurement above a predetermined value will evidence a normal pregnancy, i.e., a pregnancy which will proceed to term.

In the present method, if the patient sample is determined to have a concentration of H-hCG below a predetermined level, preferably about 13 ng/ml, and an ectopic pregnancy is further diagnosed utilizing a transvaginal ultrasound, an abdominal ultrasound or both a transvaginal ultrasound and an abdominal ultrasound, the patient may be desirably treated by the administration of an effective amount of an abortefacient, for example, methotrexate, misoprostol, combinations of methotrexate and misoprostol or by removing the ectopic fetus through use of a surgical technique (surgery). In the case of spontaneous abortion, the patient may be referred for counseling.

The present invention also relates to a method for identifying the existence of an ectopic pregnancy with high accuracy comprising in any order:

i. collecting a sample of whole blood, serum or urine from a female patient who is experiencing symptoms associated with ectopic pregnancy;

ii. measuring the concentration of hyperglycosylated hCG (H-hCG) in said sample; and ii. conducting a transvaginal ultrasound, an abdominal ultrasound or both a transvaginal and abdominal ultrasound on said patient if said concentration of hyperglycosylated hCG in said sample is less than a predetermined value, preferably about 13 ng/ml.

In this aspect of the present invention, as described above, an additional step may include initially using an early pregnancy test on the patient which measures hCG and/or H-hCG (preferably, the concentrations of both hCG and H-hCG equally) to determine if the patient is likely pregnant.

The present method provides a rapid and accurate determination of the existence of ectopic pregnancy in a female patient in as little as 30 minutes and generally within no more than about 2-3 hours (of course, depending upon the availability of the transvaginal and/or abdominal ultrasound).

In another method of the present invention, the existence or non-existence of ectopic pregnancy is diagnosed in a pregnant woman experiencing symptoms of an ectopic pregnancy comprising:

i. collecting a sample of whole blood, serum or urine from said pregnant woman; and ii. measuring the concentration of hyperglycosylated hCG in said sample; wherein a concentration of hyperglycosylated hCG in said serum of less than a predetermined value, preferably about 13 ng/ml, is indicative of an ectopic pregnancy and a concentration of more than the predetermined value, preferably, about 13 ng/ml, is indicative of the absence of an ectopic pregnancy.

A further aspect of the present invention relates to a method of identifying and treating an ectopic pregnancy comprising the steps of:

i. collecting a sample of whole blood, serum or urine from a female patient who is experiencing symptoms associated with ectopic pregnancy;

ii. measuring the concentration of hyperglycosylated hCG in said sample;

iii. conducting a a transvaginal ultrasound, an abdominal ultrasound or both a transvaginal and abdominal ultrasound on said patient if said concentration of hyperglycosylated hCG in said sample is less than a predetermined value, preferably about 13 ng/ml; and iv. treating said patient for an ectopic pregnancy if said hyperglycosylated hCG concentration is less than said predetermined value, preferably 13 ng/ml and said transvaginal ultrasound shows no evidence of a fetal sac or said transabdominal ultrasound shows evidence of an ectopic pregnancy.

An optional first step in the above method is the determination that the patient is pregnant by measuring hCG, H-hCG or hCG and H-hCG levels. In the case where H-hCG measurement is used to determine that the patient is pregnant and such measurement is known, that measurement may be used to determine the likelihood that the pregnancy is normal or abnormal (is ectopic or is likely to result in a spontaneous abortion) without taking a separate sample from the patient.

Still another aspect of the present invention relates to a method of identifying and treating ectopic pregnancy in a pregnant woman comprising the steps of:

i. collecting a sample of whole blood, serum or urine from the pregnant female patient who is experiencing symptoms associated with ectopic pregnancy;

ii. measuring the concentration of hyperglycosylated hCG in said sample; and iii. treating said patient for an ectopic pregnancy if said hyperglycosylated hCG concentration is less than a predetermined value, preferably 13 ng/ml.

In the present method, an ectopic pregnancy is desirably treated by the administration of an effective amount of an abortefacient, such as methotrexate, misoprostol, combinations of methotrexate and misoprostol or by removing the ectopic fetus through use of a surgical technique (surgery).

DETAILED DESCRIPTION OF THE INVENTION

The term "patient" is used throughout the specification to describe a female mammal, preferably a human, to whom the present method of diagnosing the likelihood of an abnormal pregnancy is directed. In preferred, non-veterinary aspects of the present invention, the term patient refers to a human patient.

The term "hyperglycosylated hCG" or "H-hCG" is used throughout the specification to describe a glycoprotein hormone secreted by trophoblast cells of the placenta of pregnant women. Hyperglycosylated hCG is also sometimes referred to in the literature as "invasive trophoblast antigen" or "ITA".

The term "normal" refers to a pregnancy which will likely (about 90-95% probability or higher) proceed to term and will not terminate in an ectopic pregnancy or spontaneous abortion.

The term "predetermined value" refers to a concentration of hyperglycosylated hCG which is a standard obtained from a statistically significant sample obtained from clinical results and to which a measurement of hyperglycosylated hCG in a measured sample is compared in order to determine whether a pregnancy is normal or not, as otherwise described herein. It is noted that the preferred predetermined value for use in the present method is about 13 ng/ml, which term generally refers to a concentration which has been calibrated in ng/ml using a choriocarinomma hyperglycosylated hCG standard, but such concentration can be described in alternative units, which are equivalent to ng/ml, such as mIU/ml. (IU is used to describe International Units—in the present invention 2 mIU/ml of H-hCG corresponds to approximately 0.18 ng/ml; 6 mIU/ml corresponds to approximately 0.55 ng/Ml, 1 ng/ml of H-hCG corresponds to approximately 11 mIU/ml and 13 ng/ml of H-hCG corresponds to approximately 143 mIU/ml). In the present application, the predetermined value of hyperglycosylated hCG preferably ranges from about 10 to 16 ng/ml, about 12 to 15 ng/ml or equivalent units, more preferably about 13 ng/ml within this range.

The term "antibody" shall mean an antibody, or an antigenbinding portion thereof, that binds to hyperglycosylated hCG and is used in an assay, to measure hyperglycosylated hCG. An anti-hyperglycosylated hCG antibody may be polyclonal or monoclonal and is usually a murine, rat or rabbit antibody, more preferably a murine antibody. Methods for making polyclonal and monoclonal antibodies are well known to the art. Monoclonal antibodies can be prepared, for example, using hybridoma techniques, recombinant, and phage display technologies, or a combination thereof. See, for example, Golub et al., U.S. Patent Application Publication No. 2003/0134300, published Jul. 17, 2003, for a detailed description of the preparation and use of antibodies as diagnostic or therapeutic agents. Antibodies to hCG isoforms, such as hyperglycosylated hCG, can be generated by standard means as described, for example, in "Antibodies: A Laboratory Manual" by Harlow and Lane (Cold Spring Harbor Press, 1988), which is hereby incorporated by reference.

Preferably, the antibody is a monoclonal antibody to provide the desired specificity. A useful antibody which selectively binds H-hCG includes Antibody B152 (ATCC No. HB-12467) and Antibody designated B207, described in U.S. Pat. Nos. 6,627,457; 6,500,627; 6,339,143 and 6,429,018, the relevant disclosures of which are incorporated by reference herein. Numerous other antibodies can potentially be used. The antibodies are quite useful in analyzing for concentrations of H-hCG in the method of present invention. While any method for determining the concentration of H-hCG may be used in the present method, preferably, a colorimetric or chemiluminescent antibody-based sandwich assay is used to determine H-hCG concentration. This technology is well-known in the art.

Antibodies are employed in assays in methods according to the present invention in order to measure the concentration of H-hCG in the serum, urine or whole blood. The assay employed is most preferably, a simple colorimetric sandwich assay, as described hereinbelow, which indicates a concentration of H-hCG of a predetermined value, preferably 13 ng/ml or above, based upon a colorimetric or chemiluminescent readout, but any assay which utilizes an anti-H-hCG antibody to measure H-hCG to a concentration which may be compared to a predetermined value may be used provided that it is fast and accurate. The preferred assay for use in the present invention is a qualitative colorimetric or chemiluminescent nitrocellulose based monoclonal sandwich assay as described in greater detail herein which can be used to qualitatively measure hyperglycosylated hCG in whole blood or serum above or below a predetermined value, preferably 13 ng/ml of serum. The assay is sufficiently sensitive to measure H-hCG, which level of 13 ng/ml is believed to represent approximately 143 mIU (milli International Units), well above the FDA established sensitivity of POC assays of 25 miu/ml. To determine whether a patient is pregnant, the patient's blood, serum or urine levels of hCG or preferably hCG and H-hCG are measured (most preferably hCG and H-hCG are measured equally), the result providing an indication of the likelihood of pregnancy. Once it is determined that a patient is likely pregnant or if it is known that a patient is pregnant, hyperglycosylated hCG is measured in the whole blood, serum or urine of patient and compared with a predetermined value, preferably about 10 to 16 ng/m, alternatively, about 12 to 15 ng/ml, more preferably about 13 ng/ml, to determine whether the pregnancy is normal (above the predetermined level) or abnormal (below the predetermined level). A diagnosed "abnormal" pregnancy is thereafter more fully diagnosed using ultrasound to determine whether the abnormal pregnancy is an ectopic pregnancy or a pregnancy likely to spontaneously abort to determine what therapeutic or other measures may be subsequently taken to assist the patient.

As a first step in the method, a woman suspected of being pregnant is tested to determine whether or not she is pregnant. The preferred method for testing the existence of pregnancy is a HCG/H-hCG Assay which measures these two biomarkers equally. A preferred assay of this type is that which detects regular intact hCG and intact H-hCG (not the free β form). The assay is a microtiter plate enzyme-immunometric assay measured in a 96 well microtiterplate reader. The capture antibody used is monoclonal 2119 (from Unipath Inc., London UK). This antibody is an anti-alpha subunit antibody which binds both hCG and hyperglycosylated hCG. Plating a 96 well microtiter plate requires 20 ml (0.2 ml per well). The tracer antibody used was peroxidase labeled monoclonal 4001(4001-POD), purchased ladled from the Medix division of Genzyme. The assay 96 well assay also requires 20 ml of tracer (0.2 ml/well). The 4001-POD is specific for the core or 3D area of the β-subunit (not the C-terminal peptide). The 2119 antibody was at a concentration of 3.5 mg/ml and the 4001-POD was at 1.0 mg/ml. The antibodies were then calibrated in order to ensure equal reactivity to both hCG and hyperglycosylated hCG and samples obtained from a patient are tested in this assay. This assay may be used to determine pregnancy in a patient, ancillary to or prior to measuring H-hCG in the instant method. Other methods well known in the art for testing pregnancy may also be used. One method is described in U.S. Pat. No. 6,627,457 of Pandian, et al. In this method, H-hCG concentrations are measured to determine pregnancy in a patient. After making a determination that a patient is pregnant, the concentration of H-hCG which may be known from the sample used to determine pregnancy above is compared with a predetermined value or alternatively, a second sample from the woman may then be analyzed to determine the levels of H-hCG in the sample and compared to a predetermined value as otherwise described herein.

A. Testing to Determine the Existence of a Normal Pregnancy—Results of a Study

The present method may be used to test for the existence of a normal or abnormal pregnancy in the point-of-care facility or in an over-the-counter (OTC) home pregnancy test. The typical pregnant woman who has not yet shown complications, but who has had at least one prior spontaneous abortion is preferably tested in this manner, although the method is generally applicable to any pregnant woman to determine outcome in that patient. The testing preferably may be done in a point-of-care facility by an attendant or doctor, or by the pregnant woman herself at home, but other applications are clearly anticipated by the present invention. In contrast, the typical ectopic pregnancy today case presents to the ER physician with severe pain half way between the left or right pelvic crest and the pubic synthesis. In addition to an ectopic pregnancy, the pain may be the result of anything from an ovarian cyst to pelvic inflammatory disease, to polycystic ovary, to an ovulation, to a muscle problem, to appendicitis.

We recently conducted a blind study examining the efficacy of the hCG doubling test which is typically used to test pregnancy outcome. The results for this first data set evidenced a predictive value positive of 22%, which means that the hCG doubling test will be correct in detecting a failing or ectopic pregnancy 22% of the time. It has a predictive value negative of 84%, meaning that it correctly diagnoses normal pregnancy 84% of the time. Overall, the hCG doubling test provides a correct result, whether positive or negative approximately 47% of the time. This data is similar to that reported previously (see references 1a and 2a below). Note that an hCG doubling test is meaningful and not the individual values alone (see reference 2a).

Using the exact same serum samples with which we showed the efficacy of the hCG doubling test (n=110), we (blindly) examined single samples measurements of H-hCG (also sometimes referred to as Invasive Trophoblast Antigen or ITA). H-hCG is extremely low in abnormal pregnancy, i.e., ectopic pregnancy and in pregnancies which have a high likelihood of spontaneously aborting. However, as determined in this blind study (see Table 1, below), measuring a single H-hCG result was 3½-fold better than the two points of an hCG doubling test in correctly predicting an ectopic or failing pregnancy. The move from 22% detection (hCG doubling test) to 77% detection of an abnormal pregnancy (based upon hyperglycosylated hCG measurement) is a massive and completely unexpected improvement. Note that the single point measurement of H-hCG provided a 95% detection of a normal pregnancy (an unexpectedly high result). Furthermore, this single serum test does not require a 2 day wait like the hCG doubling test—it can be done in less than 30 minutes. Overall, H-hCG was twice as good as the hCG doubling test in detecting ectopic and failures and correctly differentiating them from normal intrauterine pregnancies. In detecting normal pregnancy, hyperglycosylated hCG was significantly better than hCG doubling and may be used definitively in several minutes in contrast to the two days testing of the hCG doubling method. Applications in point-of-care facilities or for home pregnancy tests are aspects of the present invention.

The use of a single hyperglycosylated hCG test is a great improvement over current technology to determine the likelihood of a normal or abnormal pregnancy. Although professional laboratory H-hCG tests may be used, the 4-8 hour delay while those test results were determined is not fully acceptable. The preferred objective of this discovery is just one visit to the clinician and laboratory—not three. The hCG doubling test requires two visits to a blood drawing center, 2 days apart, then one visit to the physician, a day or so later to discuss the results. The present aspect of the present invention which relates to a point of care outcome pregnancy test available to determine normal versus abnormal pregnancy in the emergency room or doctor's office is clearly preferred. This would give a result as rapid as the point of care pregnancy test run in the ER or doctor's office, that identified pregnancy in the first place. The results would ideally be known in less than 10 minutes, preferably less than about 5 minutes, depending upon the design of the point-of-care test. In the case of a test which revealed a likelihood of an abnormal pregnancy, an ultrasound can be run as quickly and results noted as quickly by the appropriate physician. Thus, a patient could be diagnosed with a failing or ectopic pregnancy in as little as 20-30 minutes. The invention may be used in a point-of-care facility, at home or in a professional laboratory in place of existing tests.

Pregnancy is first detected at 4 weeks of gestation (4 weeks after missing a menses). A woman who has had a pregnancy terminated in a spontaneous abortion is at a high risk of recurrent spontaneous abortions and wants to know early in the pregnancy whether the pregnancy is normal or abnormal. All patients are excited when first pregnant and extremely concerned about the pregnancy having a favorable term outcome. Patients show signs of ectopic pregnancies generally at 5 weeks to 9 weeks of pregnancy, and there usually is no signs of an impending miscarriage beyond a sudden and very unexpected extremely heavy bleeding. Ultrasound cannot predict an impending spontaneous abortion. We observe in this blind study (n=110), that hyperglycosylated hCG levels range from 0.016 to 0.039 fold lower than normal intra-uterine pregnancy hyperglycosylated hCG levels. These levels are so much lower than normal intra-uterine pregnancy levels that they are almost absolutely different in their low magnitude in abnormal pregnancies (ectopic pregnancies and spontaneous abortion), at about 5 to 9 weeks of pregnancy. In our experience, 77% of abnormal pregnancies have hyperglycosylated hCG levels of less than 13 ng/ml at about 4-9 or about 5-10 weeks gestation, compared to just 5% of normal intrauterine pregnancies. As such, using 13 ng/ml serum hyperglycosylated hCG as a cut-off—we can detect spontaneous abortion and ectopic pregnancy with virtually 100% detection at 5% false detection rate. At hyperglycosylated hCG levels above 13 ng/ml, we can detect normal pregnancies at a predictive value of about 95%. This measurement provides a highly unexpected accuracy for a rapid POC analysis. Furthermore, these low levels include serum from patients who have not yet presented at the emergency room. These are women who gave serum samples at 5-8 weeks of gestation that had a proven ectopic pregnancy (presented at ER) up to one month later. As such, this 13 ng/ml serum hyperglycosylated hCG cut off test, not only identifies abnormal pregnancy (spontaneous abortion and ectopic pregnancy) in the ER, preferably between about 5 and 9 weeks of gestation, but can also be used in physicians offices in the prenatal care of patients, to screen in advance for an ectopic pregnancy. Furthermore, the 13 ng/ml serum hyperglycosylated hCG cut off test can predict a normal pregnancy with great confidence in pregnant women, especially in women who have had at least one prior miscarriage (spontaneous abortion).

Four applications are noted, although a number of other applications are possible: 1) for predicting normal or abnormal (i.e., ectopic pregnancy or spontaneous abortion) pregnancy in the physicians office (or prenatal care clinic); 2) for predicting normal or abnormal pregnancy (ectopic pregnancy or the likelihood of spontaneous abortion) in emergency rooms; 3). for predicting normal or abnormal pregnancy (ectopic pregnancy or the likelihood of spontaneous abortion) by a pregnant woman at home; 4) for predicting normal or abnormal pregnancy (ectopic pregnancy or the likelihood of spontaneous abortion) in a professional laboratory. In the event that an abnormal pregnancy is predicted, further testing using transvaginal or abdominal ultrasound can be accurately used to predict the existence of an ectopic pregnancy or the likelihood of a spontaneous abortion as the outcome.

The test device for determining concentration levels of H-hCG is preferably a qualitative point-of-care device. Alternatively, the device may be a qualitative home pregnancy test of similar architecture. By way of example, this test device is preferably a nitrocellulose-based colorimetric or chemiluminescent sandwich assay (nitrocellulose-based sandwich assay) or two antibody test based upon a capture antibody and a detection antibody wherein the capture and detection antibodies recognize and bind different epitopes of H-hCG, and wherein one of the antibodies (the capture antibody) is coupled to a label that produces a detectable a colorimetric or chemiluminescent signal (through a dye such as a gold-based dye) and the other antibody is anchored preferably in a nitrocellulose film layer, wherein the antibody is fixed in a line in the nitrocellulose film layer. This assay is well known in the art.

In this preferred assay, one antibody (the capture antibody) is a specific antibody to H-hCG only (does not detect hCG) and the second antibody (the detection antibody) is specific to another site on H-hCG (alpha or beta subunit). The capture antibody may be an antibody designated B152, or other antibody that detects H-hCG only and the detection antibody may be an antibody designated B207 as described in U.S. Pat. Nos. 6,500,627; 6,339,143 and 6,429,018, although a number of antibodies with similar specificity for the core structure of the β-subunit of hCG may be used. The capture antibody may be linked to dye (e.g., gold-based or other) and initially is in an upper layer material which is porous to liquid and is free to move to a lower layer when it comes into contact with liquid, such as blood or serum, which contains hyperglycosylated hCG. The capture antibody of the upper layer is free to move from the upper layer (preferably a porous sponge material) to the lower layer. The other antibody may be anchored in the nitrocellose matrix or other similar material in a shape like a line. The hyperglycosylated hCG in serum would enter the device and bind to the antibody-dye. There is an opening in the device case called the "result window", exposing any color from the dye. The hyperglycosylated hCG antibody-dye would then move into or through the nitrocellulose matrix until it reaches the anchored antibody. The result ("result line") would be a colored line in the "result window". A further line of die would be shown in the "result window". This is the "control dye line" or line generated by a dye that corresponds to the color and intensity that would be observed in the line in the "result window" from the antibody-dye: hyperglycosylated hCG: anchored antibody sandwich if blood/serum concentration was formed by exactly 13 ng/ml hyperglycosylated hCG.

If the "result line" was not as intense as the "control dye line", then hyperglycosylated hCG levels of <about 13 ng/ml are present indicating a likely pregnancy outcome failure, whether that failure is an impending ectopic pregnancy or spontaneous abortion (miscarriage). If the "result line" was similar or more intense than the "control dye line" then a favourable term outcome is predicted with a high 90-95+% accuracy. The aim would be for a test of sensitivity calibrated preferably to a hyperglycosylated hCG level of about 13 ng/ml. Note that the 13 ng/ml value is calibrated in the pregnancy test using a choriocarcinoma h-hCG standard and equivalent concentrations (using equivalent units to ng/ml) may be measured.

Two such methodologies are exemplary of the above approach. In the first methodology, antibody concentrations are adjusted such that the test only shows a positive result at a H-hCG serum concentration of 13 ng/ml or greater. In this case, a positive result would mean a normal intrauterine pregnancy and a negative result would mean an abnormal pregnancy generally requiring further analysis with ultrasound to determine if the pregnancy is an ectopic pregnancy or will spontaneously abort. This is the preferred basis for an over-the-counter (OTC) home pregnancy test.

A second, more sophisticated device/methodology would have a control line. In this aspect, a positive result is observed and is compared in intensity to a second line, or a control line, that corresponds to the exact intensity of a line given by 13 ng/ml. If the resulting test line is equal to, more distinct or darker than the control line, this would evidence the existence of a normal pregnancy. If the result line is less distinct or lighter than the control line it would be evidence of an abnormal pregnancy, either an ectopic pregnancy or a pregnancy which will spontaneously abort (miscarriage). Confirmation of the ectopic pregnancy through ultrasound would confirm the results—in the absence of confirmation of ectopic pregnancy the prognosis would be of spontaneous abortion. Appropriate treatment would then be undertaken.

Serum POC (Point of Care) or OTC Test, Patient Serum and Urine—First Data Set

TABLE 1

The hCG doubling test (2 measurements of hCG, 2 days apart), to predict pregnancy outcome, has become one of the biggest uses of hCG tests. It is now done routinely by all fertility clinics and by most pregnancy management clinics in the USA. In our study, we blindly compared a single serum hyperglycosylated hCG measurement with hCG doubling test in predicting pregnancy outcome in 110 serum samples. Predictive value positive (PVP), indicating a normal pregnancy and predictive value negative (PVN), indicating ectopic pregnancy or spontaneous abortion (miscarriage) were calculated considering USA occurrence of miscarried (16%) and ectopic (2.0%) pregnancies. Overall predictive value (OPV) is the percentage of times it gives a correct result whether positive or negative. See attached FIG. 1 - note that the detection range is from 5 weeks 0 days to 8 weeks 0 days, or the $1^{st}$ to the $4^{th}$ week following the missing of menses.

| Sensitivity | PVN | PVP | OPV |
|---|---|---|---|
| hCG, 2 serum sample doubling test | | | |
| 62% @ 56% false pos. | 22% | 84% | 47% |
| Quantitative hyperglycosylated hCG, 1 serum sample lab test | | | |
| 75% @ 5% false | 77% | 95% | 91% |
| New Quantitative POC hyperglycosylated hCG in Physician's Office, 1 serum, 13 ng/ml cut off | | | |
| 70% @ 5% false pos ($5^{th}$ to $8^{th}$ week of gestation) | 77% | 95% | 92% |

Second Data Set

Methods

In this example, we studied two independent sets of patients. The first set comprises 96 serum samples from cases in the $5^{th}$-$8^{th}$ weeks of gestation. The second set comprises 167 urine samples from separate cases in the $4^{th}$-$7^{th}$ weeks of gestation. In all cases, total hCG and H-hCG were measured using automated chemiluminescence immunoassays.

Results

Scattergrams (FIGS. 2 and 3) indicated 13 ng/ml was a pivotal point for H-hCG concentrations in both the serum and urine cases and by analogy, whole blood. This corresponded to 73% detection of failures at 2.9% false positive rate and 75% at 15% false positive rate, respectively. hCG results were compared at the corresponding serum and urine false positive rate. At these rates hCG detected 42% and 43% of failures. The two sample sets supported each other with hCG detecting 57% of the proportion of failures detected by H-hCG.

Conclusions

Measuring single sample serum H-hCG at 13 ng/ml in serum and urine samples predicts pregnancy failure significantly better that 2 day hCG doubling test and single sample hCG testing. A single laboratory test using this cut-off, a point-of-care or over-the-counter test using this as a concentration line, could simplify the assessment of pregnancy outcome.

Abbreviations hCG=Human chorionic gonadotropin

H-hCG=Hyperglycosylated Human chorionic gonadotropin

ROC=Receiver operating characteristics

Patient Samples—Serum

All volunteers were patients attending clinics in the Department of Obstetrics and Gynecology at the University of New Mexico Medical School. In all cases, once a positive pregnancy test was shown (from natural conceptions), an extra tube of blood was collected at the time of phlebotomy.

For this second data set, all patients had to be in the $5^{th}$ to $8^{th}$ complete weeks (5 weeks 0 days to 7 weeks 6 days since the start of the last menstrual period) on the day of sample collection. We examined 96 serum samples from continuously recruited patients attending clinic. Seventy serum samples were collected from patients having uneventful pregnancies as of the end of the first trimester of gestation (all ectopic pregnancies are identified by this time, as are the bulk of spontaneous abortions, 7-11). These will very likely lead to normal-term deliveries, so are called favorable outcome pregnancies. Twenty four are from pregnancies terminating in spontaneous abortion during this time, and 2 from those having ectopic pregnancies. These are together called failures. The described data were from a continuous recruitment of cases. All cases were recruited blindly with no knowledge of outcome. No selection or elimination of cases was made. Blood samples (red top vacutainer tubes) were separated after phlebotomy using a desk-top centrifuge (2,000×g). Serum was collected placed into a sterile tube and stored in a −80° C. freezer until assayed for total hCG and H-hCG.

Patient Samples—Urine

In this sample all patients were volunteers. Once a positive pregnancy test was shown (from natural conceptions), a tube of urine was collected from patients, whenever possible, while attending clinics, from the $4^{th}$ to the $7^{th}$ complete week of pregnancy (4 weeks 0 days to 7 weeks 6 days after start of last menstrual period). All cases were recruited blindly with no knowledge of outcome. A total of 167 cases were recruited. At the end of the first trimester, once outcome was known, 139 cases had favorable outcome, 20 had spontaneous abortion in the first trimester and 8 had ectopic pregnancy. No selection or elimination of cases was made.

Urine samples were frozen at −20° C. after collection and transferred daily to a −80° C. freezer. Samples were transferred on dry ice from and thawed and assayed for total hCG and H-hCG.

Laboratory Tests

All laboratory testing was performed in the USA hCG Reference Service Reference Service laboratories at University of New Mexico Health Science Center in 2004. This laboratory certified by the Department of Heath and Human Services for running clinical tests (CLIA ID #32D0972561). The consistency of laboratory tests is monitored by the College of American Pathologists (CAP #7176750-01).

Samples were retrieved from the freezer and thawed for the first time. All testing involved automated assays, using pre-formulated reagent packs. Total hCG was measured using the DPC Immulite hCG test. As published, this assay detects hCG, H-hCG and free β-subunit on an equal bases. When the concentration of pure hCG, H-hCG and free β-subunit were calibrated by absorbance at 278 nm (18), virtually identical results (H-hCG result 99% of hCG concentration) were observed between dimers using the DPC test (results in mIU/ml), and molar equivalent results using the free β-subunit preparation (21, 22).

Samples were tested for H-hCG using the Nichols Institute Diagnostics (NID) invasive trophoblast antigen H-hCG test, an immunometric assay with chemiluminescence detection (20). This assay is calibrated in ng/ml using a choriocarcinoma H-hCG standard. This standard was calibrated by NID, in a comparison of multiple concentration of pure H-hCG standard (batch C5, (18)) with a crude standard using the DPC Immulite test as described above. Since this standard has not been fully characterized, all hCG (mIU/ml) and H-hCG (ng/ml) values remain independent, and cannot be directly compared in common units (20, 22).

Serum and urine sample were both diluted with the provided DPC and NID diluents. As previously published, both tests can be used with serum and urine samples without a matrix effect (20-22).

Data Analysis

Total hCG and H-hCG data for all samples were entered into a Microsoft Excel 2003 spreadsheet (Microsoft Inc., Redmond Wash.). Data for failure and favorable outcomes were ranked in order of concentrations and true positive (failure outcome) rates, and corresponding false positive (favorable outcome) rates. Receiver operating characteristics (ROC) curves were plotted and areas under curves, 95% confidence intervals, asymptotic standard errors (ASE) and ROC curve t statistics were calculated using AccuROC software, version 2.4 (Accumetric Corp., Motreal, QC). Scattergram of H-hCG concentrations against gestational age were plotted using Sigma Plot software, version 9.0 (Systat Inc., Richmond Calif.). Predictive values were calculated in Mircosoft Excel assuming that 16% of clinically-recognized pregnancies end in spontaneous abortion and 2% in ectopic pregnancy in the USA, or 18% are failures (12-15).

Results

Figure 2:
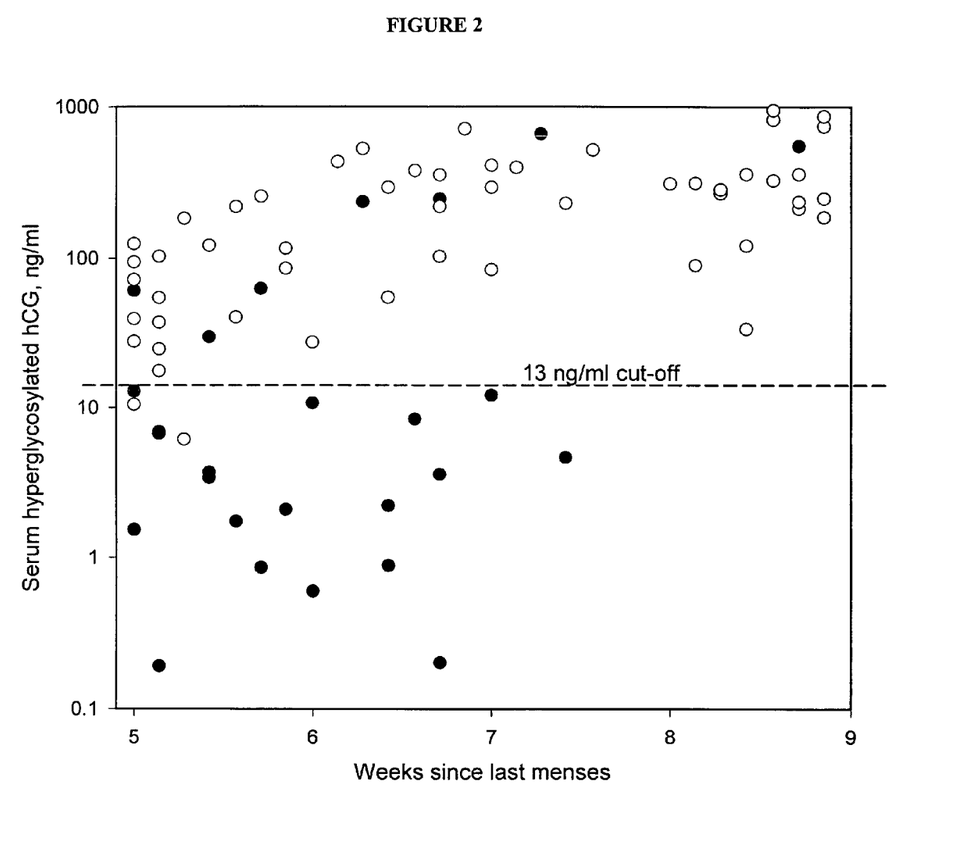
FIG. 2 is a scatter plot of individual hyperglycosylated hCG serum measurements of a second data set from normal (○) and failing pregnancies (●) in the $5^{th}$-$8^{th}$ compete weeks of gestation. The horizontal dashed line is drawn at a pivotal point, 13 ng/ml of H-hCG.
Figure 3:
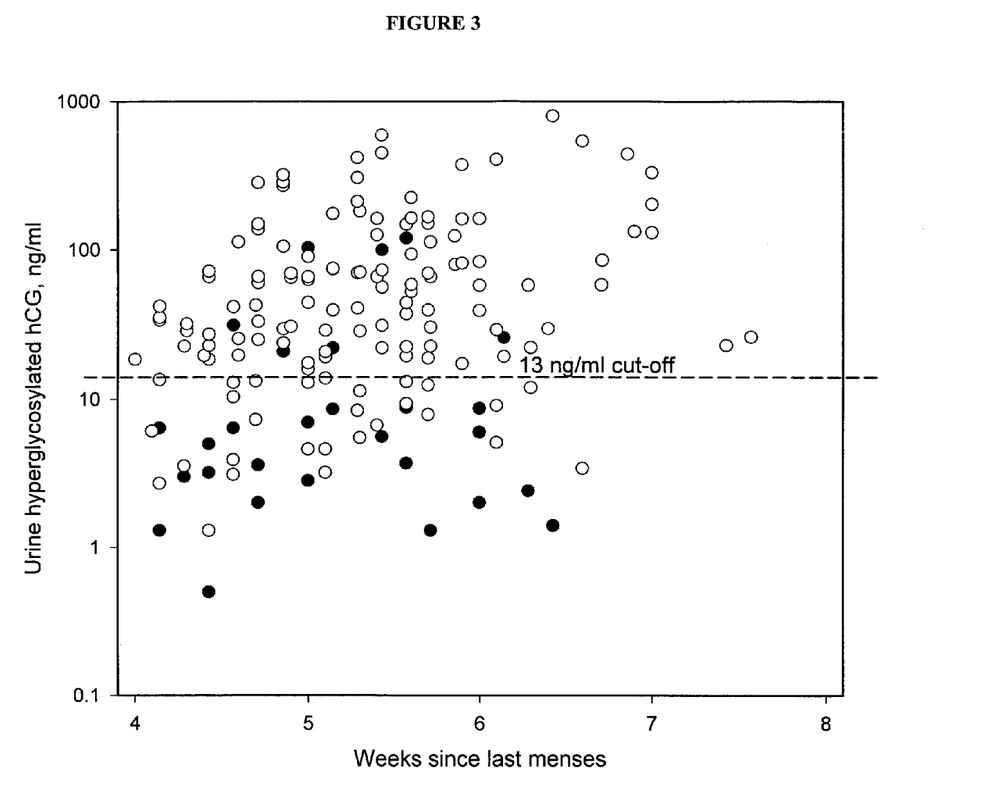
FIG. 3 is a scatter plot of individual hyperglycosylated hCG urine measurements of a second data set from normal (○) and failing pregnancies (●) in the $4^{th}$-$7^{th}$ compete weeks of gestation. The horizontal dashed line is drawn at 13 ng/ml of H-hCG.

Individual serum H-hCG concentrations were compared for serum samples from patients between the $5^{th}$-$8^{th}$ complete weeks of gestation. FIG. 2 is a scattergram of this data, with serum H-hCG results plotted according to gestational age. An ROC curve was plotted comparing all combinations of detection and false positive rate. The area under the ROC curve was 0.91±0.041 (Table 2, below). A pivotal point was apparent in the scattergram at 13 ng/ml (FIG. 2). Using 13 ng/ml cut-off, the H-hCG test detected 73% of pregnancy failures at a 2.9% false positive (favorable outcome) detection rate. This corresponded to predictive value positive (prediction of failures) of 85%.

We examined hCG concentration in these same patient samples. The area under the ROC curve was 0.87±0.048 (Table 2). We compared H-hCG data with hCG results using the matching false positive rate (2.9%). At this false positive rate hCG detected 42% of failures; the predictive value positive was 76% (Table 2).

Individual urine H-hCG concentrations were compared for serum samples from patients between the $4^{th}$-$7^{th}$ complete weeks of gestation. FIG. 2 is a scattergram of this data, with urine H-hCG results plotted according to gestational age. An ROC curve was plotted comparing all combinations of detection and false positive rate. The area under the ROC curve was 0.83±0.049 (Table 1). The 13 ng/ml cut off used for serum was also a clear discriminatory point in the urine H-hCG scattergram (FIG. 2). Using 13 ng/ml cut-off, the H-hCG test detected 75% of pregnancy failures at a 15% false positive detection rate. This corresponded to a predictive value positive (prediction of failures) of 52%.

We examined hCG concentration in these same patient samples. The area under the ROC curve was 0.74±0.047 (Table 1). A significant difference was observed between hCG and H-hCG areas, P=0.00005. We compared H-hCG data with hCG results using the matching false positive rate (15%). At this false positive rate hCG detected 43% of failures; the predictive value positive was 39% (Table 2).

Discussion

Reportedly, approximately 16% of clinically-recognized pregnancies end in spontaneous abortion and 2% in ectopic pregnancy in the USA (12-15). Early identification of pregnancy failure, as well as identification of patients who are at high risk for pregnancy failure, is important in order to provide appropriate clinical care. If a biochemical test can identify those who are at high risk, then ultrasound can be used on those selected to identify the absence of a fetal sac and identify an ectopic pregnancy. In which case early therapy (methotrexate chemotherapy or salpingectomy) can be planned to prevent the need for emergency treatment, and to avert ectopic pregnancy developing into peritonitis, which is life-threatening. If a biochemical test can identify those who are at high risk and ultrasound demonstrate in those selected a fetal sac, then patients can be prepared and trained for a likely spontaneous abortion occurrence.

The hCG 2-day doubling test is the biochemical test used today for predicting failures. This is a far from an optimal test, however, with a high false positive rate (10, 11, 27, 28). It is the experience of the University of New Mexico Reproductive Endocrinology Clinic, for instance, that this test detects 73% of failures at a 40% false-positive rate (Byrn et al., unpublished data). This test has a predictive value for detecting pregnancy failures of just 35%.

hCG values increase exponentially at 5-9 weeks of gestation. The widely changing values makes it difficult to identify a specific cut-off for hCG for detecting failing pregnancies during this period; thus the development of the 2 day doubling test (7, 9, 13, 15). It is also a cumbersome test, requiring multiple visits to the laboratory and to the physician. Urbancsek et al (28) proposed using a cut-off hCG concentration for one specific day of gestation, 50 IU/ml, and an equation for adjusting results for other days of gestation. This procedure and equation led to 75% detection of failures at 19% false positive result (predictive value 47%). This seemed a small improvement of the 2 day doubling test. Clearly, more sensitive markers were needed with a cut-off usable throughout this early period of gestation.

We investigated here a single serum sample and a single urine sample hyperglycosylated hCG measurement as markers for pregnancy outcome. Results are compared to hCG values for the same samples. As found, the ROC area under the curve values for hCG were 0.87±0.048 and 0.74±0.047 for serum and urine, respectively. Using H-hCG higher values were calculated, 0.91±0.041 and 0.83±0.049, for serum and urine, respectively. While a significant difference was observed in urine hCG and urine H-hCG testing, no significant difference was observed in serum testing (P=0.88).

Using serum samples and an H-hCG pivotal cut-off of 13 ng/ml, 73% of failing pregnancies were detected at 2.9% false positive rate. A predictive value of 85% was indicated for accuracy in detecting failing pregnancies. Using hCG and a cut-off corresponding to this same false positive rate only 42% of failures were detected; a predictive value of 76% was calculated.

Using urine samples and the H-hCG 13 ng/ml cut-off rate, 75% of failing pregnancies were detected at a 15% false positive rate. A predictive value of 52% was indicated for accuracy in detecting failing pregnancies. Using hCG and a cut-off corresponding to this same false positive rate only 43% of failures were detected; a predictive value of only 39% was calculated. Clearly, H-hCG is a very much more sensitive test than hCG for detecting failing pregnancy, using both serum and urine samples. Parallel differences were observed testing serum and urine samples, with h-hCG sensitivities of 73% and 75% for serum and urine, and hCG sensitivities of only 42% (57% of H-hCG) and 43% (57% of H-hCG). While sensitivities may be similar for serum and urine, corresponding false positive rates are approximately 5-fold higher in urine samples. This is likely due to the wide urine protein excretion variations that occur with liquid intake (5, 22, 29). These broaden the range of urine values, increasing the false positive rates.

It is concluded that single point H-hCG determinations are much more sensitive than hCG single point measurements, hCG 2 day doubling measurements (10, 11, 27, 28) and other hCG methods like those of Urbancsek et al (28), in detecting pregnancy outcome. Both serum and urine measurements can be used, with serum measurements providing a lower false positive rate and thus a better predictive value.

For this study, we examined 96 serum samples from continuously recruited patients. Seventy serum samples were collected from patients with favorable outcomes, 23 were from failing pregnancies (27%). This was the unexpected outcomes from a continuous recruitment, yet no selection or elimination of cases was made (USA incidence 16% (12-15)). We considered the possibility that these cases may be extraordinary or not representative. We also examined 167 urine samples from separately continuously recruited patients, at a separate medical center). One hundred and thirty nine urine samples were collected from patients with favorable outcomes and 20 from pregnancies leading to failures (17%). The distribution of this set of samples was much closed to the USA incidence. The results from the two sets of data were very similar, showing similar sensitivities. In both blind data sets hCG results were 57% of H-hCG results. The similarity in the data with the urine samples validates the data with the serum samples, confirming that the serum data is representative.

Currently, there are automated immunoassay tests for H-hCG available, marketed under the trade name Invasive Trophoblast Antigen (ITA) (20). Our data indicates that a single serum measurement of H-hCG would be a major improvement over two separate hCG measurements taken 2 days apart or single hCG test in assessing the risk of pregnancy outcome. One test would also be less burdensome and less time-consuming for the clinic and patient.

Costs may be limiting factor in pregnancy outcome assessment. Costs could be cut by the use of a point-of-care test that could assess risk during a single visit to a physician's office. It would also simplify and remove the burden from risk assessment, eliminating the need for formal phlebotomy and laboratory visit. A blood point-of-care test could be manufactured to produce a concentration line corresponding to the response at 13 ng/ml H-hCG. Sterile lancets could be used to obtain blood. If patient blood H-hCG was higher than 13 ng/ml, then the device would show a darker test line. Considering the statistics reported here, if patient serum H-hCG was lower than 13 ng/ml, then the device would show a fainter test line. Considering the statistics reported here, this would predict a failure outcome with 85% certainty (predictive value positive).

A point-of-care test of this kind could be run in a physician's office, providing rapid results, which could be discussed almost instantaneously. Point of care devices could also be made for testing serum or urine H-hCG with a cut-off of 13 ng/ml. The improved physician and patient convenience, combined with the greatly improved sensitivity, false positive rate and predictive statistics would likely lead to much wider use, possibly use with almost every pregnancy, than the currently used hCG 2-day doubling test.

The USA hCG Reference Service Reference Service web site is organized by the authors (hcglab.com). It is estimated that the Service receives one to two e-mails each week regarding pregnancy outcome and eagerness for results. Over-the-counter test are now available for measuring infections like cystitis, HIV, and Lyme disease, drug abuse and hyperlipidemia. A home test for assessing pregnancy outcome may be widely used, particularly by women exceptionally worried about pregnancy failure. Such tests would aid in the early detection of ectopic pregnancies and, combined with clinic ultrasound, in preparedness for ectopic pregnancy or spontaneous outcome. Our results indicate potential use of the 13 ng/ml cut-off as a control line in new over-the-counter tests. We find 75% detection at 15% false positive rate. This is better than the 73% at 40% found with 2 serum samples and the hCG doubling test, (Byrn et al., unpublished data), or the 75% detection at 19% false positive result using the single serum sample method of Urbancsek et al (28). As such a home urine test has the potential to offer improvements over today's technology.

TABLE 2

Figure 1:
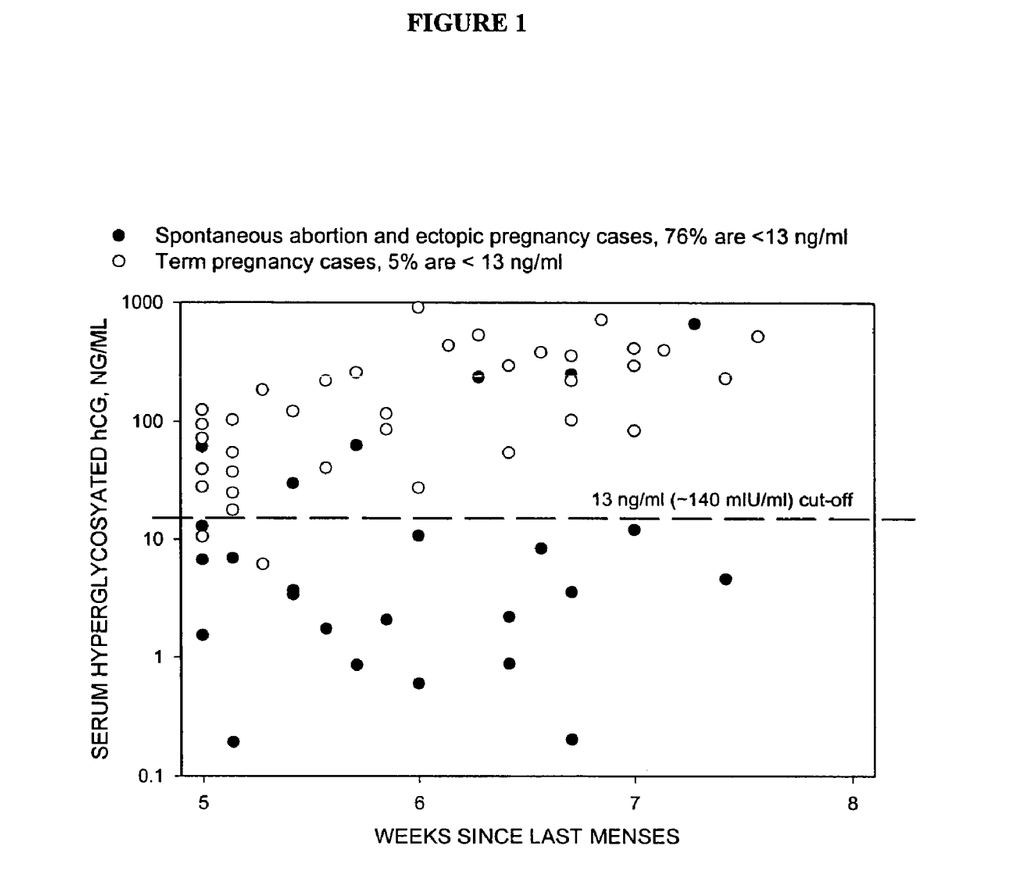
FIG. 1 is a scatter plot of individual hyperglycosylated hCG serum measurements in of a first data set from normal (○) and failing pregnancies (●). The horizontal dashed line is drawn at a pivotal point, 13 ng/ml of H-hCG.

Use of hCG and H-hCG for predicting pregnancy failure using serum and urine samples. Arbitrary cut-off values were indicated by scattergrams (FIGS. 1 and 2). False positive rates and detection rates at these cut-off values were calculated and predictive values determined. ROC statistics were calculated for serum and urine hCG and H-hCG independent of cut-off values.

|  | Serum H-hCG | Serum hCG | Urine H-hCG | Urine hCG |
| --- | --- | --- | --- | --- |
| Term outcome pregnancies | n = 70 | n = 70 | n = 139 | n = 139 |
| Cut-off concentration | 13 ng/ml | 22 mIU/ml | 13 ng/ml | 215 mIU/ml |
| Corresponding false positive rate | 2.9% | 2.9% | 15.0% | 15.0% |

TABLE 2-continued

Use of hCG and H-hCG for predicting pregnancy failure using serum and urine samples. Arbitrary cut-off values were indicated by scattergrams (FIGS. 1 and 2). False positive rates and detection rates at these cut-off values were calculated and predictive values determined. ROC statistics were calculated for serum and urine hCG and H-hCG independent of cut-off values.

|  | Serum H-hCG | Serum hCG | Urine H-hCG | Urine hCG |
|---|---|---|---|---|
| Detection Rates for Failures | | | | |
| a. All failures | 19 of 26 (73%) | 11 of 26 (42%) | 21 of 28 (75%) | 12 of 28 (43%) |
| b. Spontaneous abortions only | 17 of 24 (71%) | 10 of 24 (42%) | 14 of 20 (70%) | 9 of 20 (45%) |
| c. Ectopic pregnancy only | 2 of 2 (100%) | 1 of 2 (50%) | 7 of 8 (88%) | 3 of 8 (38%) |
| Predictive value positive | 85% | 76% | 52% | 39% |
| Area under ROC curve ± SE | 0.91 ± 0.041[1] | 0.87 ± 0.048[1] | 0.83 ± 0.049[2] | 0.74 ± 0.047[2] |
| ROC 95% confidence interval | 0.83-0.99 | 0.78-0.97 | 0.73-0.92 | 0.65-0.83 |

[1] No significant difference observed between serum hCG and serum H-hCG area under the ROC curve results ($P = 0.88$).
[2] A significant difference was observed between urine hCG and urine H-hCG area under the ROC curve results ($P = 0.00005$).

REFERENCES

1a. Urine β-core fragment, a potential screening test for ectopic pregnancy and spontaneous abortion. *Fetal Diagnosis and Therapy*, 12:336-339, 1997
2a. ITA hCG (Invasive Trophoblast Antigen, hyperglycosylated hCG) the Optimal Antigen in Pregnancy Testing. *Clinical Biochemistry*, 36(8):647-55 November, 2003.
1. Saxena B B, Hasan S H, Haour F, Schmidt-Gollwitzer M. Radioreceptor Assay of human chorionic gonadotropin: Detection of Early Pregnancy. Science 1974; 184:793-5.
2. Braunstein G D, Rasor J, Adler D, Danzen H, and Wade M E. Serum human chorionic gonadotropin levels throughout normal pregnancy. Am J Obstet Gynecol 1976; 126: 678-681.
3. Gasser R F. 1981. Embryology and fetology. In *Principles and Practice of Obstetrics and Perinatology*, Vol 1, edited by Iffy L, Kaminetzky H A (New York; John Wiley & Sons), pp. 127-80.
4. Lenton E A, Grudzinskas J G, Neal L M, Chard T, Cooke I D. Chorionic gonadotropin concentrations in early human pregnancy: Comparisons of specific and nonspecific assays. Fertil Steril 1981; 35: 40-5.
5. Wilcox A J, Baird D D, Durison D, McChesney R, Weinberg C R. Natural limits of pregnancy testing in relation to the expected menstrual period. JAMA 2001; 286: 1759-61.
6. Wilcox A J, Weinberg C R, O'Connor J F, Baird D D, Schlatterer J P, Canfield R E, et al. Incidence of early loss of pregnancy. N Engl J Med 1988; 319: 189-94.
7. Pittaway D E and Wentz A C. Evaluation of early pregnancy by serial chorionic gonadotropin determinations: A comparison of methods by receiver operating characteristic curve analysis. Fertil Steril 1985; 43: 529-533.
8. Braunstein G D, Grodin J M, Vaitukaitis J, Ross G T. Secretory rates of human chorionic gonadotropin by normal trophobiast. Am J Obstet Gynecol 1973; 115: 447-50.
9. Barnhart K, Sammel M D, Chung K, Zhou L, Hummel A C, Wensheng Gou. Decline of serum human chorionic gonadotropin and spontaneous abortion: Defining the normal curve. Obstet Gynecol 2004; 104: 975-81.
10. Liu H C, Davies O, Berkeley A, Graf M, Rosenwaks Z. Late luteal estradiol patterns are a better prognosticator of pregnancy outcome than serial beta-human chorionic gonadotropin concentrations. Fertil Steril 1991; 56: 421-6.
11. Cowan B D. Ectopic Pregnancy. Curr Op Obstet Gynecol 1993; 5: 328-32.
12. Abrar N. (May 2004) "Miscarriage: The Incidence of miscarriage" Retrieved Dec. 9, 2004, from ivf-infertility.com.
13. Sepilian V. (November 2004) eMedicine Specialties: Obstetrics and Gynecology. "Ectopic Pregnancy." Retrieved Dec. 9, 2004, from emedicine.com.
14. Jones R E. 1991. Pregnancy, Spontaneous Abortion. In *Human Reproductive Biology*, edited by Richard E. Jones. (San Diego, Calif., Academic Press, Inc.), pp. 189-228.
15. Heffner L J. 2001. Pregnancy complications, early pregnancy loss. In *Human Reproduction at a Glance*, edited by Blackwell Sciences editorial offices (Berlin, Germany, Blackwell Science Ltd.). pp. 86-91.
16. Cole L A. The O-Linked Oligosaccharide structure are striking different on pregnancy and choriocarcinoma hCG. J Clin Endocrinol Metab 1987; 65: 811-3.
17. Amano J, Nishimura R, Mochizuki M, Kobata A. Comparative study of the mucin-type sugar chains of human chorionic gonadotropin present in the urine of patients with trophoblastic diseases and healthy pregnant women. J Biol Chem 1988; 263: 1157-65.
18. Elliott M M, Kardana A, Lustbader J W, Cole L A. Carbohydrate and peptide structure of the alpha- and beta-subunits of human chorionic gonadotropin from normal and aberrant pregnancy and choriocarcinoma. Endocrine 1997; 7: 15-32.
19. Birken S, Krichevsky A, O'Connor J, Schlatterer J, Cole L, Kardana A, Canfield R. Development and characterization of antibodies to a nicked and hyperglycosylated form of hCG from a choriocarcinoma patient: Generation of antibodies that differentiate between pregnancy and choriocarcinoma hCG. Endocrine 1999; 10: 137-44.
20. Pandian R, Lu J, and Ossolunska-Plewnia J. Fully automated chemiluminometric assay for hyperglycosylated human chorionic gonadotropin (invasive trophoblast antigen). Clin Chem 2003; 49: 808-10.
21. Cole L A, Sutton J M, Higgins T N. Higgins, Cembrowski G S. Between-method variation in hCG test results, Clin Chem, 2004; 50:874-882.
22. Cole L A, Khanlian S A, Sutton J M, Davies S, Stephens N D. Hyperglycosylated hCG (invasive trophoblast antigen, ITA) a key antigen for early pregnancy detection. Clin Biochem 2003; 36: 647-55.
23. Kovalevskaya G, Birken S, Kakuma T, O'Connor J F. Early pregnancy human chorionic gonadotropin isoforms measured by an immunometric Assay for Choriocarcinoma-like hCG. J Endocrinol 1999; 161: 99-106.
24. Kovalevskaya G, Genbacev O, Fisher S J, Caceres E, O'Connor J F. Trophoblast Origin of hCG Isoforms: Cytotrophoblasts are the primary Source of Choriocarcinoma-like hCG. Mol Cell Endocrinol 2002; 194: 147-55.
25. Kovalevskaya G, Birken S, Kakuma T, Osaki N, Sauer M, Lindheim S, et al. Differential expression of human chorionic gonadotropin (hCG) Glycosylation Isoforms in failing and continuing Pregnancies: Preliminary characterization of the hyperglycosylated hCG Epitope. J Endocrinol 2002; 172: 497-506.
26. O'Connor J F, Ellish N, Kakuma T, Schlatterer J, Kovalevskaya G. Differential Urinary gonadotropin profiles in early pregnancy and early pregnancy loss. Prenat Diagn 1998; 18: 123-240.
27. Carmona F, Balasch J, Creus M, Fabregues F, Civico S, Vidal E, et al. Early hormonal marker of pregnancy outcome after in vitro fertilization and embryo transfer. J Assist Reprod Genet 2003; 20: 521-26
28. Urbancsek J, Hauzman E, Fedorcsak P, Halmos A, Devenyi N, Papp Z. Serum human chorionic gonadotropin measurements may predict pregnancy outcome and multiple gestations after in vitro fertilization. Fertil Steril 2002; 78: 540-42
29. Cole, L. A., Shahabi, S., Oz, U. A., Bahado-Singh, R. O., and Mahoney, M. J. Hyperglycosylated hCG (Invasive Trophoblast Antigen) Immunoassay: a New Basis for Gestational Down Syndrome Screening. Clin. Chem. 45:2109-2119, 1999

The invention claimed is:

1. A method for identifying the likelihood that a pregnancy is a normal pregnancy in a female patient with symptoms consistent with pregnancy comprising:
   i. determining whether the patient is pregnant; and
   ii. if the patient is pregnant, comparing a measurement of hyperglycosylated human chorionic gonadotropin (H-hCG) concentration obtained from a sample of whole blood, serum or urine from said patient at an early stage of pregnancy with a predetermined H-hCG concentration value of between about 10 ng/ml to about 16 ng/ml, wherein a measurement above said predetermined H-hCG concentration value is evidence of a normal pregnancy.

2. The method according to claim 1 wherein said sample is serum and said predetermined H-hCG concentration value is about 13 ng/ml.

3. The method according to claim 1 wherein said concentration of hyperglycosylated human chorionic gonadotropin (H-hCG) is measured using a colorimetric or chemiluminescent assay.

4. The method according to claim 3 wherein said assay is a nitrocellulose-based sandwich assay.

5. A method for identifying the likelihood of a normal pregnancy in a female patient known to be pregnant at an early stage of pregnancy comprising:
   i. collecting a sample of whole blood, serum or urine from said female patient; and
   ii. measuring the concentration of hyperglycosylated human chorionic gonadotropin (H-hCG) in said sample; and
   iii. comparing the measurement obtained in step ii with a predetermined H-hCG concentration value of between about 10 ng/ml to about 16 ng/ml, wherein a measurement of H-hCG concentration above said predetermined H-hCG concentration value is evidence of a high likelihood of a normal pregnancy.

6. The method according to claim 5 wherein said sample is serum and said predetermined hyperglycosylated human chorionic gonadotropin (H-hCG) concentration value is about 13 ng/ml.

7. The method according to claim 5 wherein said concentration of hyperglycosylated human chorionic gonadotropin (H-hCG) is measured using a colorimetric or chemiluminescent assay.

8. The method according to claim 7 wherein said assay is a nitrocellulose-based sandwich assay.

9. A method for identifying pregnancy outcome in a female patient with symptoms consistent with pregnancy comprising:
   i. collecting a sample of whole blood, serum or urine from said female patient suspected of being pregnant at an early stage of symptoms consistent with pregnancy;
   ii. determining whether the patient is pregnant by measuring concentrations of human chorionic gonadotropin (hCG), hyperglycosylated human chorionic gonadotropin (H-hCG) or both hCG and hyperglycosylated hCG in said sample; and
   iii. if the measurement in step ii shows the patient to be pregnant, comparing a measurement of hyperglycosylated hCG (H-hCG) concentration obtained from said sample or from a second sample of whole blood, serum or urine from said patient with a predetermined H-hCG concentration value of between about 10 ng/ml to about 16 ng/ml, wherein a measurement above said predetermined H-hCG concentration value is evidence of a normal pregnancy and a measurement below said predetermined H-hCG concentration value is evidence of an abnormal pregnancy.

10. The method according to claim 9 wherein said sample is serum and said predetermined hyperglycosylated human chorionic gonadotropin (H-hCG) concentration value is about 13 ng/ml.

11. The method according to claim 9 wherein said concentration of hyperglycosylated hCG (H-hCG) is measured using a colorimetric or chemiluminescent assay.

12. The method according to claim 11 wherein said assay is a nitrocellulose-based sandwich assay.

13. The method according to claim 9 wherein said abnormal pregnancy is an ectopic pregnancy.

14. The method according to claim 9 wherein said pregnancy is determined to be an abnormal pregnancy, said abnormal pregnancy is determined not to be an ectopic pregnancy, wherein said pregnancy is identified as being likely to terminate in spontaneous abortion.

15. The method according to claim 14 wherein said patient is referred for counseling.

16. The method according to claim 9 wherein said method is used in a point-of-care facility.

17. The method according to claim 9 wherein said method is used by a pregnant woman at home.

18. A method for identifying whether a female patient who presents with symptoms consistent with an ectopic pregnancy is suffering from an ectopic pregnancy, the method comprising:
   i. collecting a sample of whole blood, serum or urine from the female patient;
   ii. measuring the concentration of hyperglycosylated human chorionic gonadotropin (H-hCG in said sample;
   iii. conducting a transvaginal ultrasound, an abdominal ultrasound or a transvaginal and abdominal ultrasound on said female patient if said concentration of H-hCG in said sample is less than a predetermined H-hCG concentration value of between about 10 ng/ml to about 16 ng/ml; and iv. evaluating the results of the transvaginal ultrasound, abdominal ultrasound, or the transvaginal and abdominal ultrasound to confirm whether the female patient is suffering from an ectopic pregnancy.

19. The method according to claim 18 wherein said sample is serum and said predetermined hyperglycosylated human chorionic gonadotropin (H-hCG) concentration value is about 13 ng/ml.

20. The method according to claim 18 wherein said second step of measuring the concentration of H-hCG in said sample is also used to determine that the female patient is pregnant.

21. The method according to claim 18 wherein said concentration of hyperglycosylated human chorionic gonadotropin (H-hCG) is measured using a colorimetric or chemiluminescent assay.

22. The method according to claim 21 wherein said assay is a nitrocellulose-based sandwich assay.

23. A method for identifying the existence of an ectopic pregnancy or the likelihood of a spontaneous abortion in a female patient suspected of being pregnant comprising:
   i. collecting a sample of whole blood, serum or urine from said patient;
   ii. measuring the concentration of hyperglycosylated human chorionic gonadotropin (H-hCG) in said sample; and
   iii. conducting a transvaginal ultrasound, an abdominal ultrasound or a transvaginal and abdominal ultrasound on said patient if said measured H-hCG concentration is below a predetermined H-hCG concentration value of between about 10 ng/ml to about 16 ng/ml, wherein an ectopic pregnancy is identified by said ultrasound or the likelihood of spontaneous abortion is evidenced by the absence of ectopic pregnancy.

24. The method according to claim 23 wherein said patient is determined to be pregnant either before or after said step i.

25. The method according to claim 23 wherein said patient is determined to be pregnant either before or after said step ii.

26. The method according to claim 23 wherein said patient is determined to be pregnant using the measurement of H-hCG concentration obtained in step ii.

27. The method according to claim 23 wherein said sample is serum and said predetermined H-hCG concentration value is 13 ng/ml.

28. The method according to claim 23 wherein said concentration of H-hCG is measured using a colorimetric or chemiluminescent assay.

29. The method according to claim 28 wherein said assay is a nitrocellulose-based sandwich assay.

30. A method of determining the likelihood of the existence or non-existence of ectopic pregnancy in a pregnant woman experiencing symptoms of an ectopic pregnancy comprising:
   i. collecting a sample of whole blood, serum or urine from said pregnant woman; and
   ii. measuring the concentration of hyperglycosylated human chorionic gonadotropin (H-hCG) in said sample; wherein a concentration of hyperglycosylated hCG in said whole blood, serum or urine of less than a predetermined H-hCG concentration value of between about 10 ng/ml to about 16 ng/ml is indicative of an ectopic pregnancy and a concentration of H-hCG which is more than the predetermined H-hCG concentration value is indicative of the absence of an ectopic pregnancy.

31. The method according to claim 30 wherein said predetermined hyperglycosylated human chorionic gonadotropin (H-hCG) concentration value is 13 ng/ml.

32. The method according to claim 30 wherein said concentration of H-hCG is measured using a calorimetric or chemiluminescent assay.

33. The method according to claim 32 wherein said assay is a nitrocellulose-based sandwich assay.

34. A method of identifying and treating an ectopic pregnancy comprising the steps of:
   i. collecting a sample of whole blood, serum or urine from a female patient experiencing symptoms associated with ectopic pregnancy;
   ii. measuring the concentration of hyperglycosylated human chorionic gonadotropin (H-hCG) in said sample;
   iii. conducting a transvaginal ultrasound, an abdominal ultrasound or a transvaginal and abdominal ultrasound on said patient if said concentration of H-hCG in said sample is less than a predetermined H-hCG concentration value of between about 10 ng/ml to about 16 ng/ml;
   iv. evaluating the results of the transvaginal ultrasound, abdominal ultrasound, or the transvaginal and abdominal ultrasound to confirm whether said patient is suffering from an ectopic pregnancy; and
   v. treating said patient for an ectopic pregnancy if it is determined based on step iv. that said patient suffers from an ectopic pregnancy.

35. The method according to claim 34 wherein said sample is serum and said predetermined hyperglycosylated human chorionic gonadotropin (H-hCG) concentration value is 13 ng/ml.

36. The method according to claim 34 further comprising determining, prior to step ii, whether the female patient is pregnant.

37. The method according to claim 34 wherein said concentration of hyperglycosylated human chorionic gonadotropin (H-hCG) is measured using a colorimetric or chemiluminescent assay.

38. The method according to claim 37 wherein said assay is a nitrocellulose-based sandwich assay.

39. The method according to claim 34 wherein said treating step comprises administering an effective amount of an abortefacient to said patient or surgically treating said ectopic pregnancy.

40. The method according to claim 39 wherein said abortefacient is methotrexate, misprostol or mixtures, thereof.

* * * * *